US010141171B2

(12) United States Patent
La Marca et al.

(10) Patent No.: US 10,141,171 B2
(45) Date of Patent: Nov. 27, 2018

(54) METHOD AND KIT FOR DETERMINING METABOLITES ON DRIED BLOOD SPOT SAMPLES

(71) Applicant: AZIENDA OSPEDALIERO UNIVERSITARIA MEYER, Florence (IT)

(72) Inventors: Giancarlo La Marca, Florence (IT); Chiara Azzari, Scandicci (IT); Massimo Resti, Vaiano Prato (IT)

(73) Assignee: AZIENDA OSPEDALIERO UNIVERSITARIA MEYER, Florence (IT)

( * ) Notice: Subject to any disclaimer, the term of this patent is extended or adjusted under 35 U.S.C. 154(b) by 0 days.

(21) Appl. No.: 14/969,065

(22) Filed: Dec. 15, 2015

(65) Prior Publication Data

US 2016/0172175 A1    Jun. 16, 2016

Related U.S. Application Data

(62) Division of application No. 13/517,316, filed as application No. PCT/EP2010/070517 on Dec. 22, 2010, now Pat. No. 9,234,894.

(30) Foreign Application Priority Data

Dec. 23, 2009 (IT) .................. FI2009A0272

(51) Int. Cl.
 *G01N 33/49* (2006.01)
 *H01J 49/04* (2006.01)
 (Continued)

(52) U.S. Cl.
 CPC ........ *H01J 49/0459* (2013.01); *G01N 33/492* (2013.01); *G01N 33/66* (2013.01); *H01J 49/005* (2013.01)

(58) Field of Classification Search
 None
 See application file for complete search history.

(56) References Cited

PUBLICATIONS

Ito, T. et a. Rapid Screening of High-Risk Patients for Disorders of Purine and Pyrimidine Metabolism Using HPLC-Electrospray Tandem Mass Spectrometry of Liquid Urine or Urine-soaked Filter Paper Strips, 2000, Clinical Chemistry, vol. 46(4), pp. 445-452.*

(Continued)

*Primary Examiner* — Xiaoyun R Xu
(74) *Attorney, Agent, or Firm* — Ohlandt, Greeley, Ruggiero & Perle, LLP

(57) ABSTRACT

A method for individuating with high sensitivity and specificity ADA metabolites from dried blood spot. The method described herein can be used to extract Adenosine and Deoxyadenosine from a sample under conditions that permit concurrently extracting other metabolites, such as amino acids, free carnitine, or acylcarnitines. For example, harsh extraction conditions (such as extreme acidity and high temperature) can be avoided. The method can be used, along with other neonatal screenings, on blood samples and preferably on dried blood spots (Guthrie cards) and more preferably on Guthrie cards obtained in the II-IV day of life. The method is reliable and reproducible, easy to perform and gives a definitive response within a short time (1-2 days). One or more kits for use in the method of the disclosure are also described.

13 Claims, 3 Drawing Sheets

(51) Int. Cl.
*G01N 33/66* (2006.01)
*H01J 49/00* (2006.01)

(56) References Cited

PUBLICATIONS

Wuyts, B. et al. Critical sample pretreatment in monitoring dried blood spot citrulline, 2007, Clinica Chimica Acta, vol. 386, pp. 105-109.*

Mee, J.M.L. et al. Quantitative Analysis of Blood Amino Acids and Fatty Acids by Direct Mass Spectrometry, 1978, Recent Developments in Mass Spectrometry in Biochemistry and Medicine, Plenum Press, New York.*

Jacomelli, et al., "Simple non-radiochemical HPCL-linked method for screening for purine metabolism disorders using dried blood spot", Clinica Chimica Acta, vol. 324, No. 1-2, Oct. 2002, pp. 135-139.

Ito, et al., "The application of HPLC/ESI tandem mass spectrometry on urine-soaked filter-paper strips for the screening of disorders of purine and pyrimidine metabolism", Journal of Inherited Metabolic Disease, vol. 23, No. 4, Jun. 2000, pp. 434-437.

Koller, et al., "An essay deoxyadenosine and adenosine in human plasma by HPCL", Biochemical Medicine, Academic Press, San Diego, CA, US, vol. 24, No. 2, Oct. 1, 1980, pp. 179-184.

International Search Report and Written Opinion dated Feb. 23, 2011 for corresponding International Patent Application No. PCT/EP2010/070517.

La Marca, et al., "Tandem mass spectrometry, but not T-cell receptor excision circle analysis,identified newborns with late-onset adeosine deaminase deficiency", J Allergy Clin. Immunol., vol. 131, No. 6, Jun. 2013, pp. 1604-1610.

* cited by examiner

METHOD AND KIT FOR DETERMINING METABOLITES ON DRIED BLOOD SPOT SAMPLES

CROSS-REFERENCE TO RELATED APPLICATIONS

This application is a divisional of U.S. patent application Ser. No. 13/517,316 filed Jun. 20, 2012, which claims priority to PCT Application PCT/EP 2010/070517 filed Dec. 22, 2010 which, in turn, claims priority to Italian Patent Application No. FI 2009 A 000272 filed Dec. 23, 2009, all of which are incorporated by reference as if fully set forth herein.

FIELD OF THE INVENTION

The present disclosure is related to a method and kit for determining metabolites on dried blood spot samples (like Guthrie cards), in particular said metabolites include also those due to a defect of adenosine deaminase (ADA) or purine-nucleoside phosphorilase (PNP) defect.

BACKGROUND

Severe combined immunodeficiency (SCID) is a group of severe disease which affect immune system. Infants with SCID are healthy at birth but die of recurrent severe infection in infancy unless adequate therapy is provided. Unfortunately, most infants with SCID are not identified in the pre-infection period: the diagnosis is usually hypothesized when a severe infection occurs. At that time, however, even though a correct therapeutic intervention is started, damages due to the severe infection (such meningitis, encephalitis, severe pneumonia) can already be present and permanent sequelae can be an important burden both for the patients and the family, and society.

SCID due to a defect of adenosine deaminase (ADA) or purine-nucleoside phosphorilase (PNP) is an inherited disorder of purine metabolism. Genetic deficiency of the purine salvage enzyme ADA results in varying degrees of immunodeficiency, ranging from neonatal onset severe combined immunodeficiency to late onset immunodeficiency which can determine severe compromise of lung function in adolescents or adults.

In its typical form, the absence of the enzyme ADA allows accumulation of toxic metabolites resulting on one side on severe defect of immune system and, on the other, on permanent damage of other organs and systems such as brain or liver. In these cases SCID-ADA is fatal within the first months of life if untreated and is associate with severe sequelae is treated late.

Late onset ADA-SCID has also been described. In these cases the patients experience severe recurrent infections and chronic lung disease during infancy or adolescence. Very similar are the clinical consequences of PNP defect.

In both cases hematopoietic stem cell transplant is curative, but dependent on a good donor match. Enzyme replacement therapy is available and determines the elimination of toxic metabolites and a good reconstitution of the immune system. Gene therapy is also an option for patients. In any case, whichever therapy is chosen, it should be started as soon as possible after birth in order to obtain good therapeutic effect. Therefore diagnostics methods which allow to make a sure diagnosis in the first days of life are extremely important.

Early diagnosis of ADA-deficiency is necessary because opportune therapies (stem-cell transplantation, enzyme replacement therapy) can be curative while the disease is rapidly fatal if not treated. Diagnosis can be made searching for ADA enzyme activity or for accumulation of metabolites due to ADA deficiency.

Evaluating ADA activity is complex and sometimes can give misleading results: actually a severe defect in ADA activity can be found in subject with an absolutely normal immune function, because variable residual ADA activity expressed in cells different from immune cells can be sufficient to maintain correct immune function. For this reason dosage of metabolites is absolutely mandatory to achieve the diagnosis of immunodeficiency due to ADA or PNP deficiency. Moreover dosage of metabolites allows monitoring the reduction of their toxic activity after starting enzyme replacement therapy.

Measurement of purine and pyrimidine metabolites presents complex problems for separations. Different methods for measurement are used in clinical practice, ranging from HPLC to thin-layer chromatography. Other methods include capillary electrophoresis and even reverse-phase HPLC with electrospray ionisation tandem mass spectrometry.

However all these methods are applied on urine samples and are used when a clinical suspicion of immunodeficiency has already been formulated because of the onset of severe infections. This is a serious drawback of the methods, since affected infants should be diagnosed before onset of infections to maximize opportunity of life-saving treatment. Family history can help in performing and early diagnosis but data obtained in the USA show that only 18% affected patients have a positive family history. The number is probably even lower in Italy where most families have only one child.

The use of mass spectrometry (MS) in clinical laboratories is very much increased on the outset of the 21th century. This development is obviously due to great advances in mass spectrometry applications in the last fifteen years. Mass spectrometry permits a very rapid measurement of different metabolites in different biological specimens using filter paper spots or directly in different biological fluids. Because of its high sensitivity, this technique can be used for qualitative and quantitative analysis of many analytes such as purines and pyrimidines, amino acids and acylcarnitines, homocysteine, orotic acid, succinylacetone etc., with appropriate internal standards.

MS is extensively used for analysis of metabolites from dried blood spots taken at birth (Guthrie-cards) but among the detected metabolites those due to ADA deficiency are not detected because the methods of extraction are not effective. The classical method commonly used for expanded newborn screening is performed by using a C1-3 linear or branched chain monoalcohol (preferably methanol) (Millington D S, et al. J Inherit Metab Dis. 1990; 13(3):321-4; Donald H. et al. Clin. Chem., November 2003; 49: 1797-1817; la Marca G, et al. Rapid Commun Mass Spectrom. 2003; 17(23): 2688-92).

Aim of the present disclosure is to provide an analytical method that could allow also the determination of purine and pyrimidine metabolites (including in particular ADA or PNP deficiency metabolites) along with the determination of other metabolites that are commonly determined for metabolites screening, especially those screening performed on dried blood spot taken at birth.

DEFINITIONS AND ABBREVIATIONS

ADA: adenosine deaminase
Ado: Adenosine

D-Ado: Deoxyadenosine
MS: mass spectrometry
PNP: Purine-nucleoside phosphorilase
SCID: Severe combined immunodeficiency

SUMMARY OF THE INVENTION

Object of the present disclosure is a method able to individuate, by means of MS, with high sensitivity and specificity purine and pyrimidine metabolites (including especially ADA or PNP deficiency metabolites) from dried blood. The method described herein can be used to extract Adenosine and Deoxyadenosine from a dried blood sample under conditions that permit concurrently extracting other metabolites, such as other purines and pyrimidines, amino acids, free carnitine, or acylcarnitines. The method of the disclosure is characterised by the use of an extraction mixture comprising a mixture of water and C1-3 linear or branched chain monoalcohol (preferably methanol) wherein water is present at least at 10% v/v. The method can be used, along with other neonatal screenings, on dried blood spots, preferably absorbed on cardboard, and more preferably on Guthrie cards, even more preferably those Guthrie cards obtained in the II-IV day of life, or during enzyme replacement therapy (to monitor the efficacy of therapy).

The method is reliable and reproducible, easy to perform and gives a definitive response within a short time (1-2 day). The method allows avoiding, harsh extraction conditions (such as extreme acidity and high temperature).

It offers, for the first time, the possibility to get the diagnosis of ADA-SCID at birth, before onset of infectious disease. Early diagnosis of SCID allows treating the affected patients very soon so avoiding severe complications due to infectious disease which are always expected in the follow-up of immune-deficient patients. Human and monetary costs of long hospitalisation, intensive care, and early death which are a result from delayed SCID diagnosis could be avoided diagnosing the affected patient at birth by the method herein described.

Further object of the disclosure is a kit, kits useful for preparing samples for detection and/or measurement (using tandem mass spectrometry) of Adenosine and Deoxiadenosine along with multiple other analytes (e.g., other purines and pyrimidines, amino acids, free carnitine, and acylcarnitine) in a dried blood sample.

DETAILED DESCRIPTION

Figure 1A:
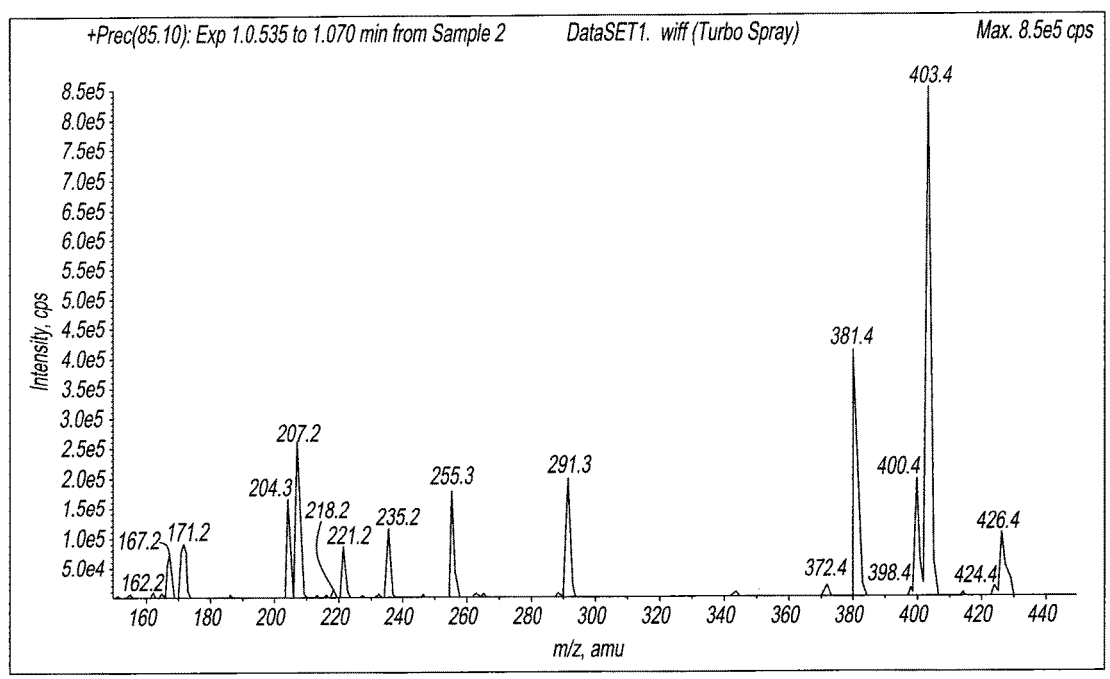
FIG. 1a shows a precursor scan of m/z 85 were several acylcarnitines are detected from the sample (panel A)

The disclosure features methods for extracting Adenosine and Deoxiadenosine along with one or more additional analytes (e.g., other purines and pyrimidines, amino acids, acylcarnitines, and free carnitine) from the sample in a single step such that the concentrations of Adenosine and Deoxiadenosine and one or more additional analytes (e.g., other purines and pyrimidines, amino acids, free carnitine, and acylcarnitines) in the extract reflect their respective concentrations in the sample.

Following the extraction, the presence or amount of Adenosine and Deoxiadenosine can be determined along with one or more additional analytes (e.g., free carnitine, acylcarnitines, and amino acids) using mass spectrometry (e.g., tandem mass spectrometry).

The method can include contacting a sample with an extraction solution containing a C 1-3 linear or branched chain monoalcohol (e.g., methanol, ethanol, propanol, or isopropanol) and water.

Adenosine and Deoxiadenosine are not soluble in absolute alcohol or in a solution containing less than 10% of water. To extract (release) Adenosine and Deoxiadenosine along with one or more additional analytes from a sample (e.g., a biological sample such as a blood spot) in a single step, the sample can be contacted with an extraction solution containing a C 1-3 linear or branched chain monoalcohol (e.g., methanol, ethanol, propanol, or isopropanol) with at the least 10% of water.

Preferably the method of the disclosure is performed adding the extraction solution in two steps: in the first step contacting the sample with a C 1-3 linear or branched chain monoalcohol corresponding to 100-x % v/v of the final volume; in the following second step adding to the sample water corresponding to x % v/v of the final volume v/v; wherein x is the v/v water percentage varying from 10 to 90%.

Preferably the extraction solution contains 30-50% v/v of water; more preferably The best analytical condition is obtained when an extraction solution containing methanol 60% and water 40%. Moreover, the maximum yield for the extraction of Adenosine and Deoxiadenosine is obtained when the addition of extraction solution is performed in two following steps: in the first step contacting the sample with a methanol corresponding to 60% v/v of the final volume. In the following second step adding to the sample water corresponding to 40% v/v of the final volume v/v. The first step fixed proteins, peptides and haemoglobin to the cellulose of the Guthrie card reducing consistently their extraction. Proteins, peptides and haemoglobin could be relevant interference in mass spectrometry analysis. The method can also include contacting the sample directly with an extraction solution containing methanol and water 60/40 v/v. But in this case the concentration of water can be such that the extraction solution reconstitutes some of the proteins and peptides while at the same time dissolving other analytes (e.g., Adenosine, Deoxiadenosine, acylcarnitines, free carnitine, and amino acids) present in the sample. The extraction solution can also contain an organic acid such as acetic and/or formic acid at a concentration of 1-5 mM (preferably 2.5-3.5 mM).

The extraction solution can also, optionally, contains one or more internal standards for, e.g., amino acids, free carnitine, acylcarnitines and Adenosine and Deoxiadenosine at known concentrations.

The sample mixture can then be incubated for a predetermined period of time of at least 15 minutes (and preferably no more than 120 minutes) to allow the extraction of amino acids, free carnitine and acylcarnitines as well as the extraction of Adenosine and Deoxiadenosine.

The extract can then be transferred to an unused well of a micro titer plate and the samples then analyzed by tandem mass spectrometry, optionally, with the aid of a liquid handling device for sample injection.

The instrumental settings on the tandem mass spectrometer are then set to detect the respective metabolites of interest (amino acids, acylcarnitines, free carnitine, and Adenosine and Deoxiadenosine) as well as their corresponding internal standards in a multiplex fashion.

Additional analytes that can be detected and/or measured with Adenosine and Deoxiadenosine include, e.g., alanine, arginine, citrulline, glycine, leucine, methionine, ornithine, phenylalanine, proline, tyrosine, valine, and acylcarnitines such as Free, Acetyl, Acrylyl, Propionyl, Butyryl, Tiglyl, Isovaleryl, 3-OH-butyryl, Hexenoyl, Hexanoyl, 3-OH-Isovaleryl, Heptanoyl, Octenoyl, Octanoyl, Nonanoyl, Malonyl, Decatrienoyl, Decadienoyl, Decenoyl, Decanoyl, Methylmalonyl, Glutaryl, 3-OH-Decanoyl, Dodecenoyl, Dodecanoyl, Dehyroadipyl, Adipyl, 3-OH-Dodecanoyl, Tetradecadienoyl, Tetradecenoyl, Myristoyl, Dehydrosuberyl, Suberyl, 3-OH-Tetradecanoyl, Hexadecenoyl, Palmitoyl, Dehydrosebacyl, Sebacyl, 3-OH-Hexadecanoyl, Linoleyl, Oleyl, Stearoyl. Other purines and pyrimidines include but are not limited to Uracil, Cytosine, Thymine, Adenine, Guanine, Uridine, Cytidine, Thymidine, Guanosine, Hypoxanthine, Deoxyguanosine, Deoxyinosine, Deoxyuridine, 5-OH-Me-uracil, AICAR (Aminoimidazole-4-carboxamide ribotide), Dihydrouracil, β-Alanine, Inosine, Uric acid, Orotic acid, ☐-Aminoisobutyric acid, Dihydrothymine, Ureidopropionate, Xanthine, SAICAr (Succinyl-aminoimidazole-4-carboxamide riboside) and Succinyl-adenosine.

Mass Spectrometry

Tandem mass spectrometry can be used to detect and/or measure Adenosine and Deoxiadenosine and one or more additional analytes (e.g., free carnitine, acylcarnitines, and amino acids) in a sample (e.g., a biological sample). In tandem mass spectrometry, two mass analyzers are linked in series via a collision cell. The first mass analyzer (first quadrupole) is used to select an ion of interest (e.g., an ion of a particular mass-to-charge ratio (m/z)). The selected ions are then transferred to a collision cell where they are fragmented by collisions with an inert gas (e.g., nitrogen or helium or argon). This process is called collisionally-activated dissociation (CAD) and is performed in the Collision Cell of the Mass Spectrometer. Once the precursor ions have fragmented, the second mass analyzer (third quadrupole) is used to scan and detect all of the produced product ions, or to select and detect particular fragment ions.

Figure 1B:
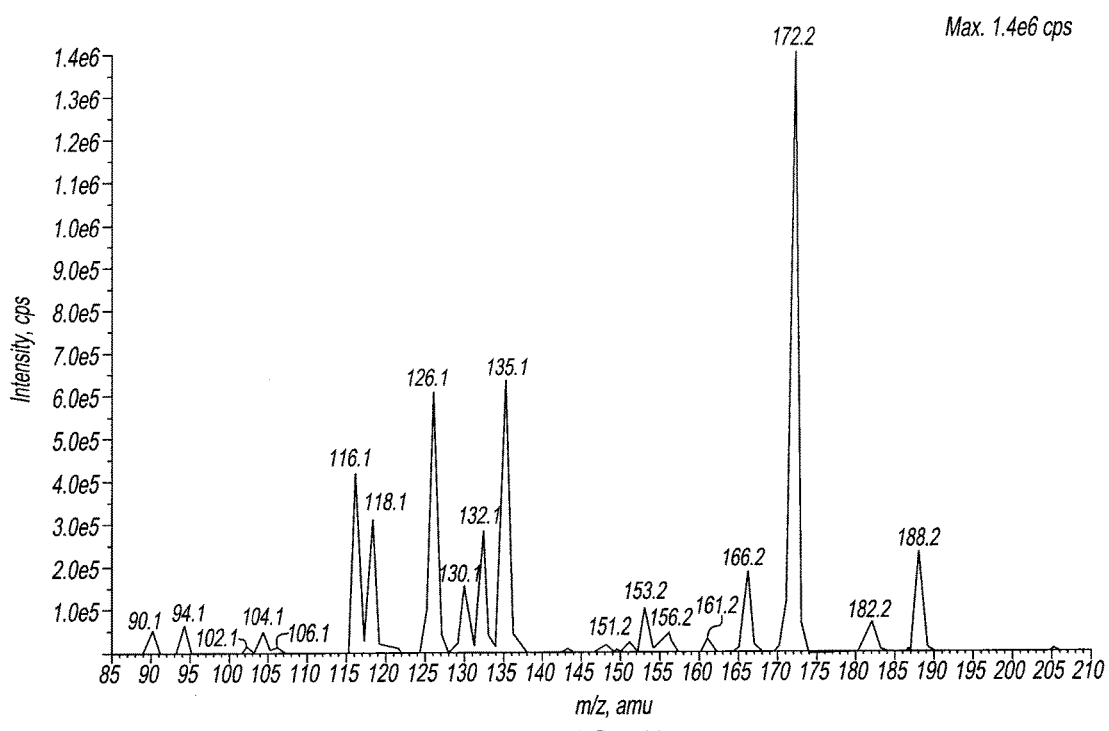
FIG. 1b shows a neutral loss scan of m/z 46 were several amino acids are detected from the same sample (panel B)
Figure 1C:
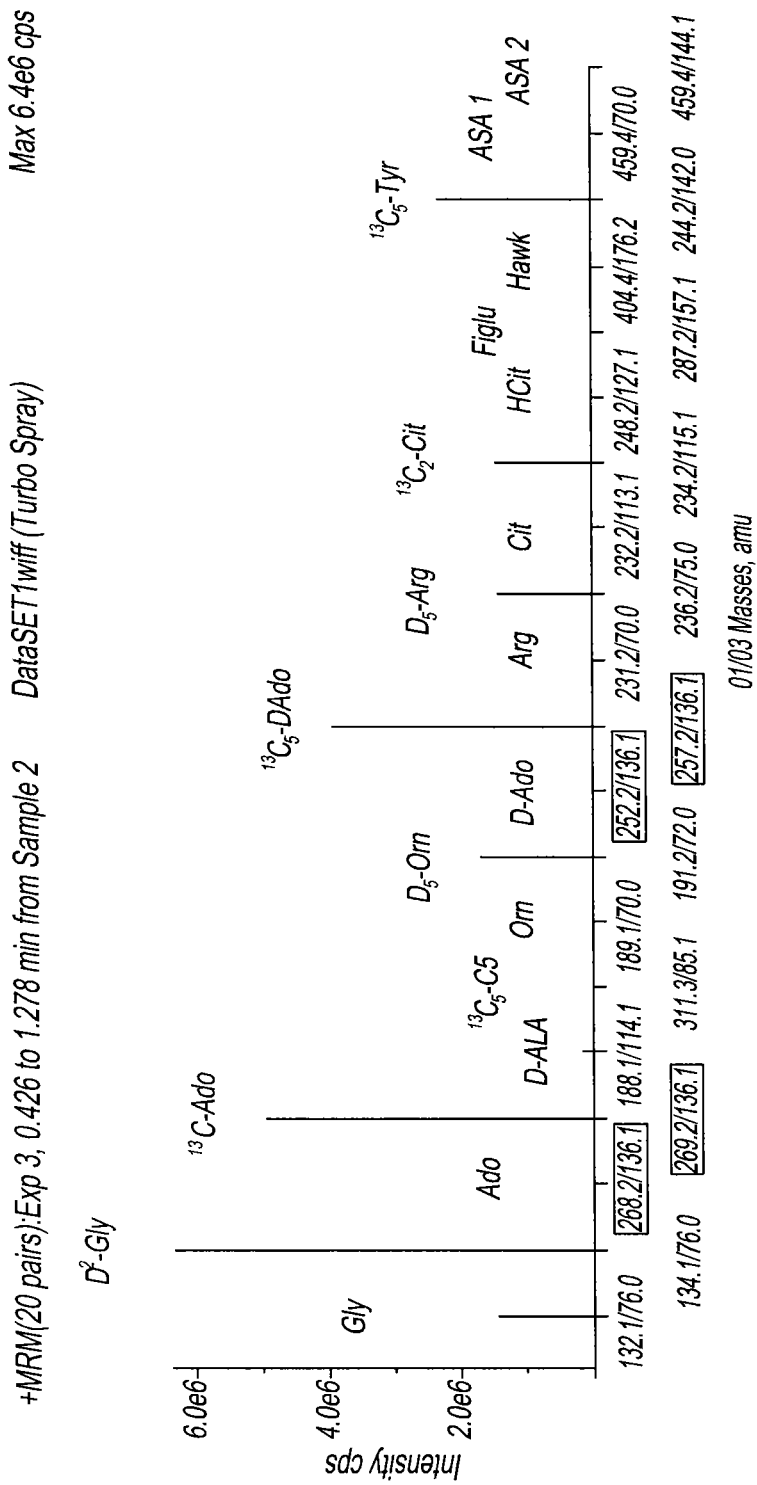
FIG. 1c shows a scan of where internal standards, stable heavy isotope analogs of the Adenosine and Deoxiadenosine were also present in the sample (Panel C).

As detailed in the accompanying Examples, tandem mass spectrometry was used to ionize the precursor molecules of Adenosine and Deoxiadenosine and several amino acids, fragment the ions, and detect specific peaks that are indicative of the presence of these molecules in the sample. The tandem mass spectrometry detection can be accomplished in a number of ways. In one type of tandem mass spectrometry (commonly performed on triple quadrupole tandem mass spectrometers) ions that fragment to produce common product (fragment) ions can be detected as a class by performing a "precursor ion scan", whereby selecting the appropriate mass for the common fragmention in the Collision Cell, all ion that produce the common fragment ions are detected. This type of scan can be used to detect the acylcarnitines in a sample (precursor ion of m/z 85 scan). In a different form of tandem mass spectrometry, ions that fragment to produce a common neutral loss can be detected as a class by performing a so called neutral loss scan where by setting an appropriate mass offset equal to the common neutral loss between first and third quadrupoles all ions that fragment to produce the specified neutral loss are detected. This type of scan is performed to detect amino acids in a sample (neutral loss of m/z 46 if the analytes in the extracted sample were unbutylated esters). FIG. 1 shows a neutral loss scan of m/z 46 where several amino acids are detected from the same sample and a precursor scan of m/z 85 were several acylcarnitines are detected from the sample. In yet another type of tandem mass spectrometry known as multiple reaction monitoring (MRM), a precursor ion of interest is selected in the first quadrupole, fragmented in the collision cell and a specific fragment ion resulting from the collisional activation is selected in the third quadrupole and finally detected.

First and third quadrupoles are fixed to respectively select the corresponding precursor and fragment ion pairs of interest for a predetermined amount of time (a few milliseconds). If additional analytes need to be detected, additional detection transitions can be introduced in the experiment. The data from all selected mass transitions can be acquired sequentially to obtain the desired information. The detection and quantitation of Adenosine and Deoxiadenosine in a mixture can be obtained by employing the specific mass transition for each of these compounds as follows: for Adenosine: first quadrupole fixed to select and transmit the precursor ion at m/z 268, third quadrupole fixed to select and transmit the specific product ion at m/z 136 (MRM transition 1); for Deoxiadenosine: first quadrupole fixed to select and transmit the precursor ion at m/z 252, third quadrupole fixed to select and transmit the specific product ion at m/z 136 (MRM transition 2). These two MRM transitions can be measured sequentially from the same sample for a predetermined amount of time to detect the presence and/or concentration of a mixture of these compounds in such sample.

Stable isotope-labelled internal standards for Adenosine and can be added to a sample, by which quantitation of Adenosine and Deoxiadenosine, and thus Adenosine and Deoxiadenosine itself, can be performed. Such labelling of derivatized Adenosine and Deoxiadenosine with stable isotopes results in a mass shift, while retaining very similar physicochemical properties between the labelled and unlabelled compounds. Generally, one or more internal standards can be added at known concentration to a sample to allow for quantitation of the analyte of interest (e.g., Adenosine and Deoxiadenosine). For example, for a sample analyzed using tandem mass spectrometry, the ratio of the signals produced by Adenosine and Deoxiadenosine and its corresponding internal standard can be used to determine the amounts of this compound in the sample. The internal standard can also be added to distinguish naturally occurring (endogenous) molecules. As above, the internal standards can be prepared in an extraction solution prior to mixing a sample (e.g., a blood sample) and the extraction solution. Alternatively, the internal standards can be added to the mixture at any step in the sample preparation that ensures these internal standards will not be removed from the mixture during the sample processing (e.g. after a liquid-liquid extraction or a solid phase extraction). Internal standards for an analyte of interest (or other molecules, e.g., biomolecules described herein) detected by a method described herein can be any modification or analog of that analyte molecule that is detectable by mass spectrometry. An internal standard is separately detectable from the molecule based on unique physical characteristics, such as a unique mass or mass-to-charge ratio. A commonly used internal standard for mass spectrometry is a stable isotopically labelled form or chemical derivative of an analyte of interest (e.g., if the analyte Adenosine and Deoxiadenosine, the internal standard can be an isotopically labelled Adenosine and Deoxiadenosine). The same for additional analytes herein described and reported as amino acids and acylcarnitines. For example, stable isotope labelled analogs can be used to quantitate the corresponding analyte of interest using the technique known as isotope dilution mass spectrometry where the analyte and internal standards are processed in the same sample. Internal standards can be designed such that 1) the labelling causes a shift in mass of at least 1 mass unit and 2) that none of the stable isotope labels are located in labile sites to prevent exchange. Labels can be $^2$H (D), $^{15}$N, $^{13}$C or $^{18}$O in any combination. The actual location of the labels on the molecule can vary provided the prerequisite 2 (above) is satisfied. Moreover, the position of the labels and the potential change in the mass of the fragment ions can also be used to confirm separation of the internal standard and analytes. Examples of potential internal standards useful in the methods described herein include, but are not limited to, an isotopically labelled: Adenosine and Deoxiadenosine (e.g., Ribosine-1-$^{13}$C-Adenosine and $^{13}$C$_5$ Deoxiadenosine), carnitine, acylcarnitine, or amino acid (e.g., phenylalanine, citrulline, glutamic acid). The detection of specific labelled internal standard in a mixture can be obtained by employing the specific mass transition for each of these compounds as follows: for Ribosine-1-$^{13}$C-Adenosine: first quadrupole fixed to select and transmit the precursor ion at m/z 269, third quadrupole fixed to select and transmit the specific product ion at m/z 136 (MRM transition 3); for $^{13}$C$_5$ Deoxiadenosine: first quadrupole fixed to select and transmit the precursor ion at m/z 257, third quadrupole fixed to select and transmit the specific product ion at m/z 136 (MRM transition 4).

Samples

Suitable samples for the methods described herein include dried blood absorbed onto a paper or polymer substrate.

Validation of the Method

Three pairs of dried blood spots (Guthrie cards) from three patients with SCID-ADA have been obtained from those stored in Neonatal Screening Center of the Tuscany region. All the patients had been diagnosed in the first year of life using conventional methods on urine or blood samples obtained with venipuncture. Diagnosis was confirmed using genetic analysis of DNA. All the parents of the 3 patients resulted carriers for the gene mutation associated with SCID-ADA.

The method described in the present disclosure allowed detection of toxic metabolites of ADA in all 3 cases, with quantitative analysis. The levels of the toxic metabolites were 10.000-30.000 times higher than levels found in normal subjects. The method was also applied to 5000 dried blood spot from healthy subjects. In none of them an increased level of toxic metabolites of ADA were found. In summary, the results obtained with the method of the disclosure show that SCID-ADA can be diagnosed with highest sensitivity (100%) and specificity (100%) from dried blood spot taken at birth through a triple-quadrupole mass spectrometer with TurbolonSpray source.

Therefore, the technology described herein is applicable to screening, diagnosis, prognosis, monitoring therapy and compliance, and any other application in which determining the presence or amount of panels of two or more biomolecules, such as Adenosine and Deoxiadenosine and one or more of an amino acid, free carnitine, or an acylcarnitine, is useful.

Kits

Also provided herein are kits useful for preparing samples for detection and/or measurement (using tandem mass spectrometry) of Adenosine and Deoxiadenosine along with multiple other analytes (e.g., other purines and pyrimidines, amino acids, free carnitine, and acylcarnitine) in a dried blood sample.

The kits can include one or more internal standards and/or controls for use in subsequent mass spectrometric analysis. For example, the kits can include Adenosine and Deoxiadenosine as a control and a derivatized form of labeled (e.g., isotope labelled) Ribosine-1-$^{13}$C-Adenosine and $^{13}$C$_5$ Deoxiadenosine) as an internal standard. The Adenosine and Deoxiadenosine and/or derivatized Adenosine and Deoxiadenosine can each be provided in the kit in a liquid or dried (e.g., lyophilized) form. The Adenosine and Deoxiadenosine can be provided in an amount of 0.1-5 mmol. The kits can include Adenosine and Deoxiadenosine in a container containing one or more additional controls or internal standards. For example, the kit can include a container with a Adenosine and Deoxiadenosine control, one or more amino acid controls, and one or more carnitine (e.g., free carnitine and acylcarnitines) controls.

One or more solutions contained in the kit can be stored in, e.g., silanized glass vials. One or more components of the kit can be stored in a container that prevents or minimizes loss of material or evaporation of a solvent. For example, the container can be sealed with a septum.

The kits can include, e.g., dried blood spots useful as a control. For example, the dried blood spot can be enriched with one or more analytes (e.g., one or more analytes at known concentrations) such as Adenosine and Deoxiadenosine, one or more amino acids, free carnitine, or one or more acylcarnitines.

The kits can also, optionally, include an extraction solution such as any of the extraction solutions described herein. The extraction solution can contain a C 1-3 linear or branched monoalcohol with the at least 25% of water. The kits can also include one or more solvent solutions containing, e.g., acetonitrile or isopropanol. The solvent solutions can also contain water, e.g., a solvent solution containing 80% acetonitrile and 20% water.

EXPERIMENTAL SECTION

Examples

Example 1

Reference standard blood (whole blood) spots were prepared using a pooled whole blood obtained from 5 subjects. The blood was processed by adjusting the hemoglobin concentration to 17 mg/dL and adding to the blood Adenosine and Deoxiadenosine at known concentrations. The processed blood was dispensed onto filter paper cards to form blood spots on the filter paper matrix. Each blood spot was generated by dispensing 25 µL of processed blood. The blood spots were allowed to dry overnight.

A small disc 3.2 mm of a dried blood spot was punched and deposited in a well of a micro well plate. The sample was extracted by dispensing 200 µL of an extraction solution that consisted of a mixture of methanol and water at an approximate relative volume-to-volume ratio of 60% methanol and 40% water. Internal standards, stable heavy isotope analogs of the Adenosine and Deoxiadenosine were also present in the extraction solution. The internal standards included in the solution are indicated in tandem mass spectrometry scan shown in FIG. 1

Example 2

Reference standard blood (whole blood) spots were prepared using a pooled whole blood obtained from 5 subjects.

The blood was processed by adjusting the hemoglobin concentration to 17 mg/dL and adding to the blood several amino acids, carnitine, acylcarnitines and Adenosine and Deoxi-adenosine at known concentrations. The processed blood was dispensed onto filter paper cards to form blood spots on the filter paper matrix. Each blood spot was generated by dispensing 25 μL of processed blood. The blood spots were allowed to dry overnight.

A small disc 3.2 mm of a dried blood spot was punched and deposited in a well of a micro well plate. The sample was extracted by dispensing 200 μL of an extraction solution that consisted of a mixture of methanol and water at an approximate relative volume-to-volume ratio of 60% methanol and 40% water. Internal standards (stable heavy isotope analogs of the analytes of interest) for several amino acids, carnitine, acylcarnitines and Adenosine and Deoxiadenosine were also present in the extraction solution. The extracted sample was injected into an electrospray triple quadrupole tandem mass spectrometer with the aid of an automated liquid handling device. Mass spectral data for the amino acids were acquired via a neutral loss scan of 46 Da. Mass spectral data for the Adenosine and Deoxiadenosine were acquired via a Multiple Reaction Monitoring. The definition for each of the analytes can be found in Table 1). The percentage of each analyte recovered was determined through comparison with an internal standard for each analyte.

The imprecision of the assay was determined by analyzing the samples described in table 1. Each sample run consisted of sextuplicate punches of each sample which were processed and measured as described in Example 2. The study included six such runs a day for a total of six days. With this information the following imprecision components were determined: within run, between run -within day, and between day from which the total imprecision was determined. The results of the imprecision analysis of Adenosine and Deoxiadenosine are shown in Table 2.

These data demonstrate that the methods described herein can be used to simultaneously extract and quantify Adenosine and Deoxiadenosine, amino acids, carnitine, acylcarnitines using tandem mass spectrometry.

TABLE 1

| Compound Name | Symbol | [M + H]+ | Butylated Mass |
|---|---|---|---|
| Purines | | | |
| Adenosine | Ado | 268.2 | |
| Deoxi-Adenosine | D-Ado | 252.2 | |
| Aminoacids | | | |
| Alanine | Ala | 90.0 | 146.1 |
| Alloisoleucine | Allo-Ile | 132.1 | 188.2 |
| Arginine | Arg | 175.1 | 231.2 |
| Argininosuccinic acid | Asa | 291.1 | 459.3 |
| Asparagine | Asn | 133.1 | 189.1 |
| Aspartic acid | Asp | 134.0 | 246.2 |
| beta-Alanine | | 90.0 | 146.1 |
| Citrulline | Cit | 176.1 | 232.2 |
| Glutamic acid | Glu | 148.1 | 260.2 |
| Glutamine | Gln | 147.1 | 203.1 |
| Glycine | Gly | 76.0 | 132.1 |
| Histidine | His | 156.1 | 212.1 |
| Hydroxyproline | HO-Pro | 132.1 | 188.1 |
| Isoleucine | Ile | 132.1 | 188.2 |
| Leucine | Leu | 132.1 | 188.2 |
| Lysine | Lys | 147.1 | 203.2 |
| Methionine | Met | 150.1 | 206.1 |
| Ornithine | Orn | 133.1 | 189.2 |
| Phenylalanine | Phe | 166.1 | 222.2 |
| Proline | Pro | 116.1 | 172.1 |
| Pyroglutamic Acid | | 130.0 | 186.1 |
| Tyrosine | Tyr | 182.1 | 238.1 |
| Valine | Val | 118.1 | 174.2 |
| Succinylacetone | SA | 155.1 | 211.2 |
| Formiminoglutamic Acid | Figlu | 231.2 | 287.2 |
| Homocitrulline | Hcit | 190.1 | 246.2 |
| Hawkinsine | Hawk | 348.3 | 404.4 |
| Deltaaminolevulinic Acid | D-AL | 122.1 | 188.1 |
| Acylcarnitines | | | |
| Free | C0 | 162.1 | 218.2 |
| Acetyl | C2 | 204.1 | 260.2 |
| Acrylyl | C3:1 | 216.1 | 272.2 |
| Propionyl | C3 | 218.1 | 274.2 |
| Butyryl | C4 | 232.2 | 288.2 |
| Tiglyl | C5:1 | 244.2 | 300.2 |
| Isovaleryl | C5 | 246.2 | 302.2 |
| 3-OH-butyryl | C4-OH | 248.1 | 304.2 |
| Hexenoyl | C6:1 | 258.2 | 314.2 |
| Hexanoyl | C6 | 260.2 | 316.3 |
| 3-OH-Isovaleryl | C5-OH | 262.2 | 318.2 |
| Heptanoyl | C7 | 274.2 | 330.3 |
| Octenoyl | C8:1 | 286.2 | 342.3 |
| Octanoyl | C8 | 288.2 | 344.3 |
| Nonanoyl | C9 | 302.2 | 358.3 |
| Malonyl | C3DC | 248.1 | 360.2 |
| Decatrienoyl | C10:3 | 310.2 | 366.3 |
| Decadienoyl | C10:2 | 312.2 | 368.3 |
| Decenoyl | C10:1 | 314.2 | 370.3 |
| Decanoyl | C10 | 316.2 | 372.3 |
| Methylmalonyl | C4DC | 262.1 | 374.2 |
| Glutaryl | C5DC | 276.1 | 388.3 |
| 3-OH-Decanoyl | C10-OH | 332.2 | 388.3 |
| Dodecenoyl | C12:1 | 342.3 | 398.3 |
| Dodecanoyl | C12 | 344.3 | 400.3 |
| Dehyroadipyl | C6:1DC | 288.1 | 400.3 |
| Adipyl | C6DC | 290.2 | 402.3 |
| 3-OH-Dodecanoyl | C12-OH | 360.3 | 416.3 |
| Tetradecadienoyl | C14:2 | 368.3 | 424.3 |
| Tetradecenoyl | C14:1 | 370.3 | 426.4 |
| Myristoyl | C14 | 372.3 | 428.4 |
| Dehydrosuberyl | C8:1DC | 316.2 | 428.3 |
| Suberyl | C8DC | 318.2 | 430.3 |
| 3-OH-Tetradecanoyl | C14-OH | 388.3 | 444.4 |
| Hexadecenoyl | C16:1 | 398.3 | 454.4 |
| Palmitoyl | C16 | 400.3 | 456.4 |
| Dehydrosebacyl | C10:1DC | 344.2 | 456.3 |
| Sebacyl | C10DC | 346.2 | 458.4 |
| 3-OH-Hexadecanoyl | C16-OH | 416.3 | 472.4 |
| Linoleyl | C18:2 | 424.3 | 480.4 |
| Oleyl | C18:1 | 426.4 | 482.4 |
| Stearoyl | C18 | 428.4 | 484.4 |

TABLE 2

| Investigated Metabolite | Spiking nmoles/L | Intra-day precision (n = 6) % | Inter-day precision (n = 6) % | Readings Average uMoles/L | Accuracy n = 6 |
|---|---|---|---|---|---|
| Adenosine | 0 | 0 | 0 | 0.0 | 0.0 |
| Adenosine | 33 | 3.5 | 3.1 | 34.0 | 103.1 |
| Adenosine | 165 | 4.9 | 3.7 | 158.0 | 95.8 |
| Adenosine | 330 | 7.8 | 6.0 | 336.2 | 101.9 |
| Adenosine | 3300 | 3.8 | 4.8 | 3299.7 | 100.0 |
| Adenosine | 6600 | 2.1 | 2.6 | 6594.2 | 99.9 |
| Adenosine | 9900 | 2.3 | 2.0 | 9899.9 | 100.0 |
| Deoxi- | 0 | 0 | 0 | 0.0 | 0.0 |

TABLE 2-continued

| Investigated Metabolite | Spiking nmoles/L | Intra-day precision (n = 6) % | Inter-day precision (n = 6) % | Readings Average uMoles/L | Accuracy n = 6 |
|---|---|---|---|---|---|
| Adenosine Deoxi-Adenosine | 33 | 19.6 | 16.9 | 32.8 | 92.9 |
| Deoxi-Adenosine | 165 | 6.6 | 4.8 | 169.6 | 100.3 |
| Deoxi-Adenosine | 330 | 5.2 | 3.6 | 325.4 | 100.6 |
| Deoxi-Adenosine | 3300 | 5.6 | 6.7 | 3300.2 | 100.3 |
| Deoxi-Adenosine | 6600 | 3.4 | 3.4 | 6599.2 | 100.0 |
| Deoxi-Adenosine | 9900 | 3.1 | 3.1 | 9904.9 | 100.0 |

What is claimed is:

1. A kit specially designed to be used for the preparation of a dried blood sample for a direct tandem MS analytical determination of Adenosine and Deoxyadenosine concurrently with more than one metabolite selected from the group consisting of amino acids, free carnitine, acylcarnitines and any combinations thereof, from said dried blood sample, said kit comprising:
    at least one container containing stable isotope-labelled Adenosine and Deoxyadenosine as internal standards and more than one additional internal standards selected from the group consisting of amino acids, acylcarnitines and free carnitine, wherein the isotope label is selected from the group consisting of $^2$H (D), $^{15}$N, $^{13}$C and $^{18}$O;
    at least one dried blood spot as a control, wherein said dried blood spot is enriched with Adenosine and Deoxyadenosine at known concentrations and enriched with one or more metabolites selected from the group consisting of amino acids, free carnitine, acylcarnitines and any combinations thereof at known concentrations; and
    at least one container containing an extraction solution comprising a C1-3 linear or branched chain monoalcohol.

2. The kit according to claim 1, wherein said dried blood spot is further enriched with one or more metabolites selected from the group consisting of purines, pyrimidines, and any combinations thereof at known concentrations.

3. The kit according to claim 1, wherein the C1-3 linear or branched chain monoalcohol in the extraction solution is methanol.

4. The kit according to claim 1, wherein the extraction solution comprises at least 10% of water.

5. The kit according to claim 1, wherein the extraction solution comprises less than 10% of water, and wherein the kit further comprises at least one container containing water.

6. The kit according to claim 1, further comprising at least one container containing Adenosine and Deoxyadenosine as controls.

7. The kit according to claim 6, wherein container containing Adenosine and Deoxyadenosine as controls also contains one or more additional controls selected from the group consisting of amino acids, acylcarnitines and free carnitine.

8. The kit according to claim 6, wherein each of the Adenosine and Deoxyadenosine is provided in an amount of 0.1-5 mmol.

9. The kit according to claim 1, further comprising a container containing a solvent solution comprising acetonitrile or isopropanol.

10. The kit according to claim 9, wherein the solvent solution further comprises water.

11. The kit according to claim 1, wherein the direct tandem MS analytical determination of Adenosine and Deoxyadenosine concurrently with a plurality of metabolites selected from the group consisting of amino acids, free carnitine and acylcarnitines provides a diagnosis of SCID from the dried blood spots, or monitors the efficacy of therapy during enzyme replacement therapy.

12. The kit according to claim 11, wherein the dried blood spots are taken on Guthrie cards obtained in the II-IV day of life of a Previously presented born baby.

13. The kit according to claim 1 wherein the tandem MS is a triple quadrupole with electrospray ion source.

* * * * *